(12) United States Patent
Tanaka (10) Patent No.: US 12,319,905 B2
(45) Date of Patent: Jun. 3, 2025

(54) MEDICAL DEVICE HAVING SPACE FOR ASSISTING IN EMBEDDING OF BIO SAMPLE IN EMBEDDING MATERIAL

(71) Applicant: Tohoku University, Sendai (JP)

(72) Inventor: Yuji Tanaka, Kofu (JP)

(73) Assignee: Tohoku University, Sendai (JP)

( * ) Notice: Subject to any disclaimer, the term of this patent is extended or adjusted under 35 U.S.C. 154(b) by 898 days.

(21) Appl. No.: 17/438,858

(22) PCT Filed: Mar. 12, 2020

(86) PCT No.: PCT/JP2020/010942
§ 371 (c)(1),
(2) Date: Sep. 13, 2021

(87) PCT Pub. No.: WO2020/189528
PCT Pub. Date: Sep. 24, 2020

(65) Prior Publication Data
US 2022/0154118 A1    May 19, 2022

(30) Foreign Application Priority Data
Mar. 15, 2019   (JP) .................................. 2019-048434

(51) Int. Cl.
*G01N 1/36*       (2006.01)
*A61F 2/14*       (2006.01)
(Continued)

(52) U.S. Cl.
CPC ................. *C12M 3/04* (2013.01); *A61F 2/14* (2013.01); *A61K 35/30* (2013.01); *A61K 35/545* (2013.01); *A61P 27/02* (2018.01)

(58) Field of Classification Search
None
See application file for complete search history.

(56) References Cited

U.S. PATENT DOCUMENTS

| 7,595,874 B1* | 9/2009 | Pelekhaty .............. G02B 21/26 |
| | | 356/318 |
| 2005/0170383 A1* | 8/2005 | Wu ........................ B01L 3/5027 |
| | | 435/6.16 |

(Continued)

FOREIGN PATENT DOCUMENTS

| JP | 2000-266744 A | 9/2000 |
| JP | 2015535607 A | 12/2015 |

OTHER PUBLICATIONS

International Search Report mailed Jun. 9, 2020, issued in corresponding International Application No. PCT/JP2020/010942, filed Mar. 12, 2020, 2 pages.

(Continued)

*Primary Examiner* — Holly Kipouros
(74) *Attorney, Agent, or Firm* — Christensen O'Connor Johnson Kindness PLLC (57) ABSTRACT

It was difficult to create a thin bio sample embedded in an embedding material without using an expensive microtome. The present invention provides a medical device having a space for assisting in the embedding of a bio sample in an embedding material, the medical device being provided with a cover part and a base part having a recessed section in which the space is created by covering the cover part, wherein the base part is provided with a flow passage having an inlet section that is in fluid communication with the space, and the flow passage is configured such that when a force is applied to the medical device so that the volume of the space decreases, the embedding material flows out while preventing a positional misalignment of the bio sample inside the embedding material.

6 Claims, 10 Drawing Sheets

(51) Int. Cl.
*A61K 35/30* (2015.01)
*A61K 35/545* (2015.01)
*A61P 27/02* (2006.01)
*C12M 3/04* (2006.01)

(56) References Cited

U.S. PATENT DOCUMENTS

| | | |
|---|---|---|
| 2015/0008616 A1* | 1/2015 | Pasternak .......... B29C 37/0053 |
| | | 425/117 |
| 2015/0289856 A1 | 10/2015 | Saqi et al. |
| 2016/0215254 A1* | 7/2016 | Meldrum .......... B01L 3/502761 |
| 2017/0067008 A1* | 3/2017 | Kiedrowski .......... C12M 23/22 |
| 2019/0120735 A1* | 4/2019 | Kinuta ................ G01N 1/4077 |
| 2019/0314003 A1 | 10/2019 | Saqi et al. |
| 2020/0157484 A1* | 5/2020 | Kozbial ................ C12M 23/22 |

OTHER PUBLICATIONS

M'Barek, K.B., et al., "Human ESC—derived retinal epithelial cell sheets potentiate rescue of photoreceptor cell loss in rats with retinal degeneration," Sci. Transl. Med.: 9 eaai7471 (2017) pp. 1-12.

\* cited by examiner

MEDICAL DEVICE HAVING SPACE FOR ASSISTING IN EMBEDDING OF BIO SAMPLE IN EMBEDDING MATERIAL

TECHNICAL FIELD

The present invention relates to a medical device having a space for assisting in embedding of a biological sample in an embedding material.

BACKGROUND ART

Age-related macular degeneration is a disease that causes vision loss due to changes in the macula caused by damage accumulated with age. The age-related macular degeneration is generally classified into two types: atrophic age-related macular degeneration which is caused by atrophy of macular tissue; and exudative age-related macular degeneration which is caused by damage to macula caused by new blood vessels just below a retina.

Anti-VEGF therapy using vascular endothelial growth factor (VEGF) is known as a treatment for the exudative age-related macular degeneration. The anti-VEGF therapy is a method for injecting VEGF into a vitreous body in order to inhibit new blood vessels, which is a commonly used treatment method.

Recently, a therapeutic method for transplanting retinal pigment epithelium (RPE) cell sheets derived from human embryonic stem (ES) cells or human induced pluripotent stem (iPS) cells into patients suffering from the exudative age-related macular degeneration has been studied (Non-Patent Document 1). In the therapeutic method disclosed in the Non-Patent Document 1, RPE cells damaged by the new blood vessels are removed along with the new blood vessels and a cultured RPE cell sheet is transplanted. Therefore, the RPE cell sheet is embedded in a hydrogel such as gelatin so that it can expand spontaneously. The hydrogel-embedded RPE cell sheet needs to be thin to facilitate injection into subretina.

RELATED ART DOCUMENT

Non-Patent Document

Non-Patent Document 1: Ben M'Barek et al, Sci. Transl. Med. 9, eaai7471 (2017)

SUMMARY OF THE INVENTION

Problem to be Solved by the Invention

In the Non-Patent Document 1, a microtome equipped with a vibrating blade is used to thinly slice a gelatin block in which RPE cell sheets are embedded. When the RPE cell sheets embedded in hydrogel are prepared by the microtome, there is a problem that the expensive microtome and skilled professionals who could handle it are required.

Means of Solving the Problem

The inventor has developed a device that can easily prepare thin hydrogel-embedded RPE cell sheets without using expensive microtomes.

The present invention is to provide a medical device having a space for assisting in embedding of a biological sample in an embedding material, the medical device including:

a lid, and
a base with a recessed part where the space is defined by covering the recessed part with the lid,
wherein the base includes a flow channel having inlets in fluid communication with the space,
the flow channel is configured to allow the embedding material to flow out while preventing misalignment of the biological sample within the embedding material when a force is applied to the medical device to reduce the volume of the space.

Such a medical device can prevent the misalignment of the biological sample in the embedding material, and can easily prepare the embedded RPE cell sheet without using the expensive microtome, and can easily retain the RPE cell sheet in the center of the embedding material.

In the medical device, the flow channel includes at least four main channels, and
each inlet of the at least four main channels is arranged apart from each other at equal angles to a center of a bottom of the recessed part Such a medical device can more stably prevent the misalignment of the biological sample in the embedding material because the channels exist in the upper, lower, left and right sides.

In the medical device, the flow channel includes one or more sub-channels in each region between the two adjacent main channels, and
each region includes the same number of the sub-channels each other.

Such a medical device can be applied to various biological samples due to the improved flexibility of channel layout.

In the medical device, the base includes a spacer being in contact with the lid, and a spacer support being in contact with the spacer, and
the spacer includes a through hole.

Such a medical device can easily manufacture the base.

In the medical device, at least a part of a surface of the spacer support being in contact with the spacer has grooves, and the flow channel is defined by covering the grooves with the spacer, or at least a part of a surface of the spacer being in contact with the spacer support has grooves, and the flow channel is defined by covering the grooves with the spacer support.

Such a medical device can easily form the flow channel.

In the medical device, the spacer is made of an elastic material.

In such a medical device, a force can be easily applied to the medical device to reduce the volume of the space.

In the medical device, the spacer support is made of a material with high thermal conductivity.

Such a medical device can more quickly cool the biological sample in the medical device.

In the medical device, the medical device further includes a holder,
the holder is a hollow body including a straight body and an overhang extending toward a center of the holder at an end of the straight body,
an inner diameter of the straight body is larger than outer diameters of the base and lid, and
an inner diameter of the overhang is smaller than the outer diameter of the lid.

In the medical device equipped with such a holder, a uniform force can be applied to the medical device.

DESCRIPTION OF EMBODIMENTS

Definition

For convenience, certain terms employed in the context of the present disclosure are collected here. Unless defined otherwise, all technical and scientific terms used herein have the same meaning as commonly understood by one of the ordinary skilled in the art to which this invention belongs. The singular forms "a", "an", and "the" are used herein to include plural referents unless the context clearly dictates otherwise.

Notwithstanding that the numerical ranges and parameters setting forth the broad scope of the invention are approximations, the numerical values set forth in the specific examples are described as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

First Embodiment

A medical device according to the present embodiment has a space for assisting in embedding of a biological sample in an embedding material. The medical device has a lid and a base with a recessed part where the space is defined by covering the recessed part with the lid. The base includes a flow channel having inlets in fluid communication with the space. The flow channel is configured to allow the embedding material to flow out while preventing misalignment of the biological sample within the embedding material when a force is applied to the medical device to reduce the volume of the space.

Figure 1:
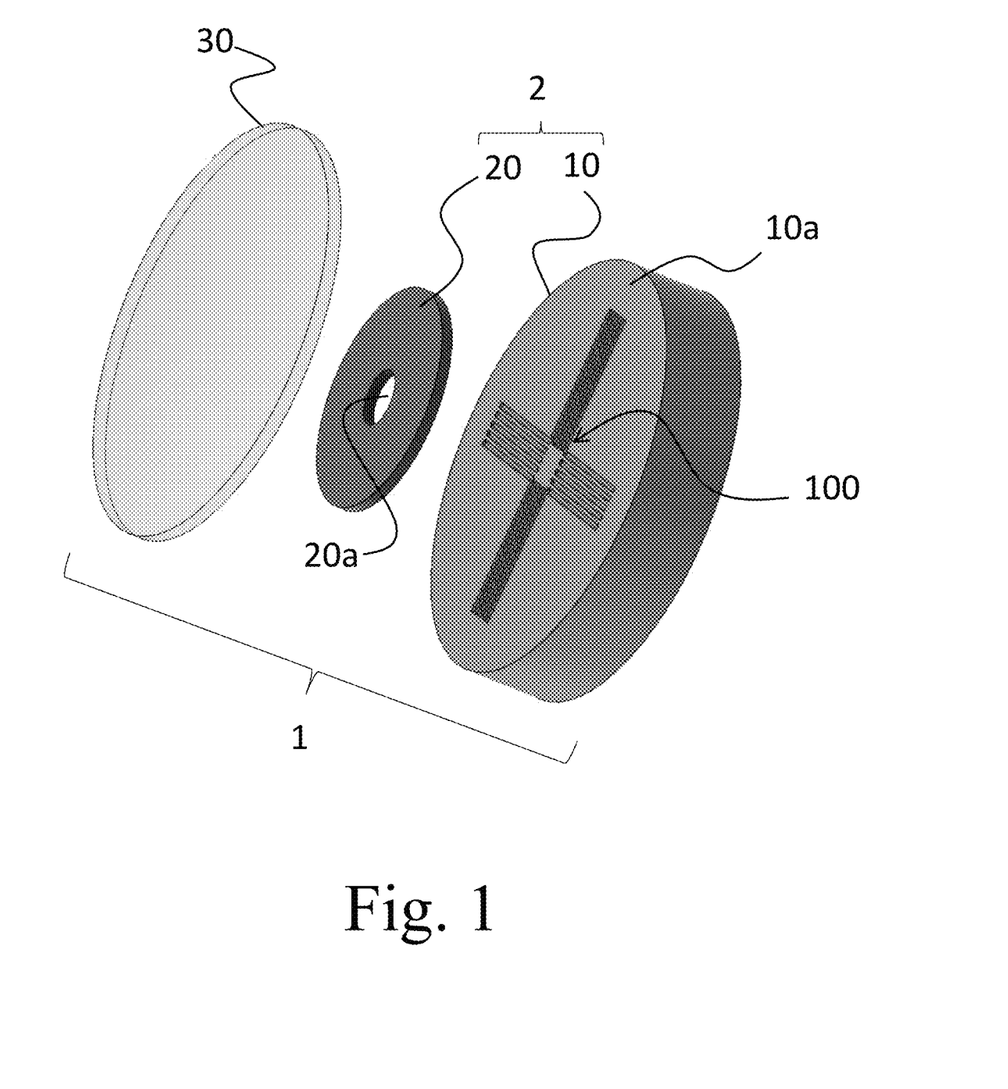
FIG. 1 shows an exploded view of a medical device having a space for assisting in the embedding of a biological sample in an embedding material, according to the present invention.

FIG. 1 shows an exploded view of a medical device 1 having a space for assisting in embedding of a biological sample in an embedding material, according to the present embodiment. In an embodiment, the medical device 1 has a base 2 and a lid part 30. The base 2 includes a spacer support 10 and a spacer 20. In the present embodiment, a surface of the spacer support 10 being in contact with the spacer 20 has grooves, and a flow channel 100 is formed by covering the grooves with the spacer 20. In another embodiment, a surface of the spacer 20 being in contact with the spacer support 10 has grooves, and a flow channel 100 is formed by covering the grooves with the spacer support 10. A through hole 20a is formed in the center of the spacer 20.

The spacer support 10 and the spacer 20 may be made of glass, metal, plastic, or a combination thereof, but they are preferably made of a material with high thermal conductivity (e.g., metal such as silicon, aluminum and stainless steel). The lid 30 may be made of glass, metal, plastic, or a combination thereof, and is preferably made of transparent glass or transparent plastic. The spacer 20 may be made of an elastic material (e.g., silicone rubber, plastic, and combinations thereof), but not limited thereto. When the spacer 20 manufactured from the elastic material has the grooves, the grooves have preferably reinforcing members to prevent deformation of the grooves when a force is applied to the medical device 1 to reduce the volume of the space 4. The reinforcing member can be, for example, a metal or plastic arch or tube. The medical device 1 may be disposable.

In the present embodiment, opening shape of the through hole 20a of the spacer 20 is circular, but it may be oval or polygonal including square.

Figure 2:
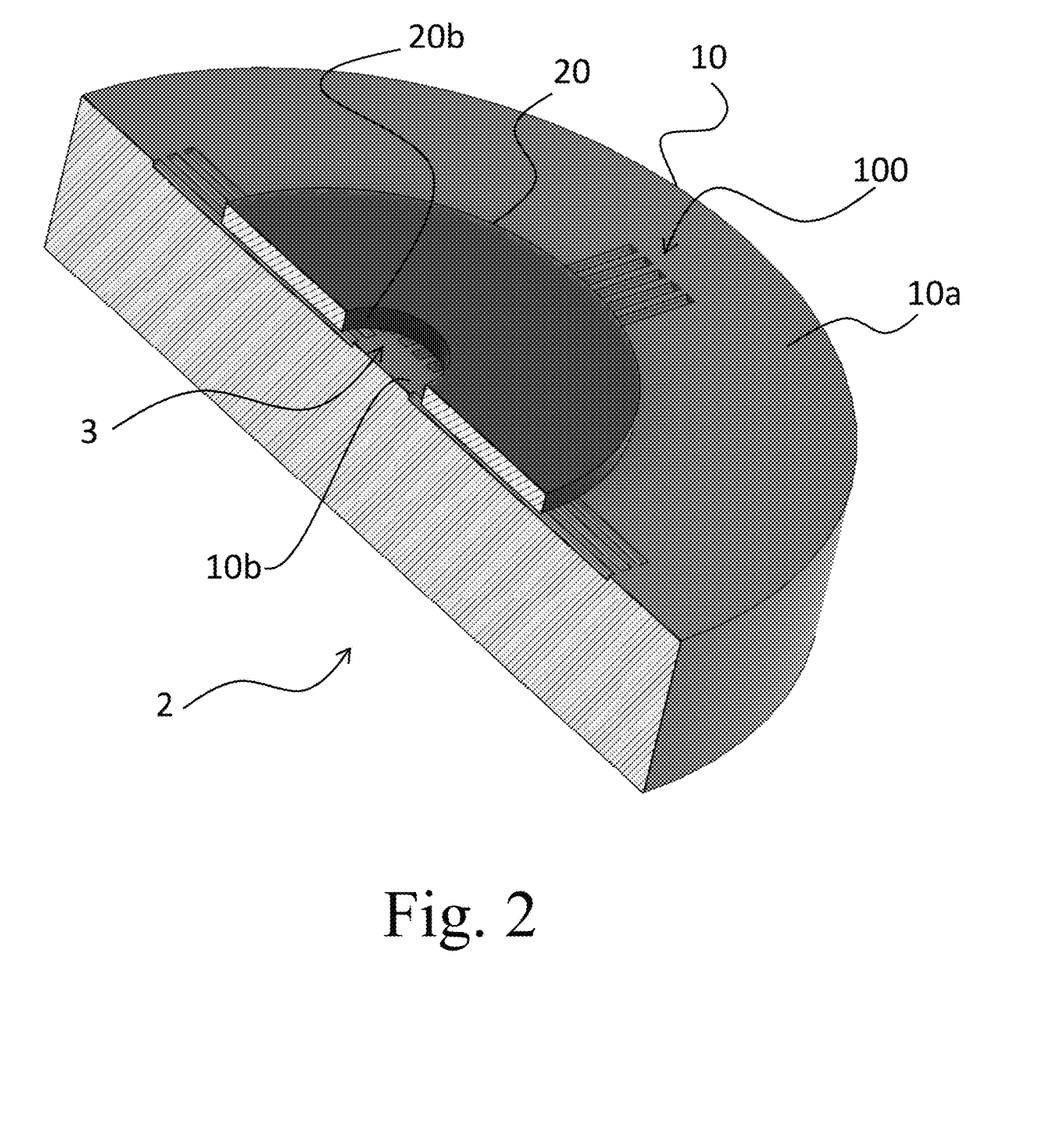
FIG. 2 shows a perspective cross-sectional view of a base with a spacer being in contact with a surface of a spacer support, according to the present invention.

FIG. 2 shows a perspective cross-sectional view of the base 2 with the spacer 20 being in contact with the surface 10a of the spacer support 10. The base 2 shown in FIG. 2 has a recessed part 3 defined by the surface 10a and an inner wall 20b of the spacer 20. A bottom of the recessed part 3 has a flat part 10b defined by the inlets of the flow channel 100.

Figure 3:
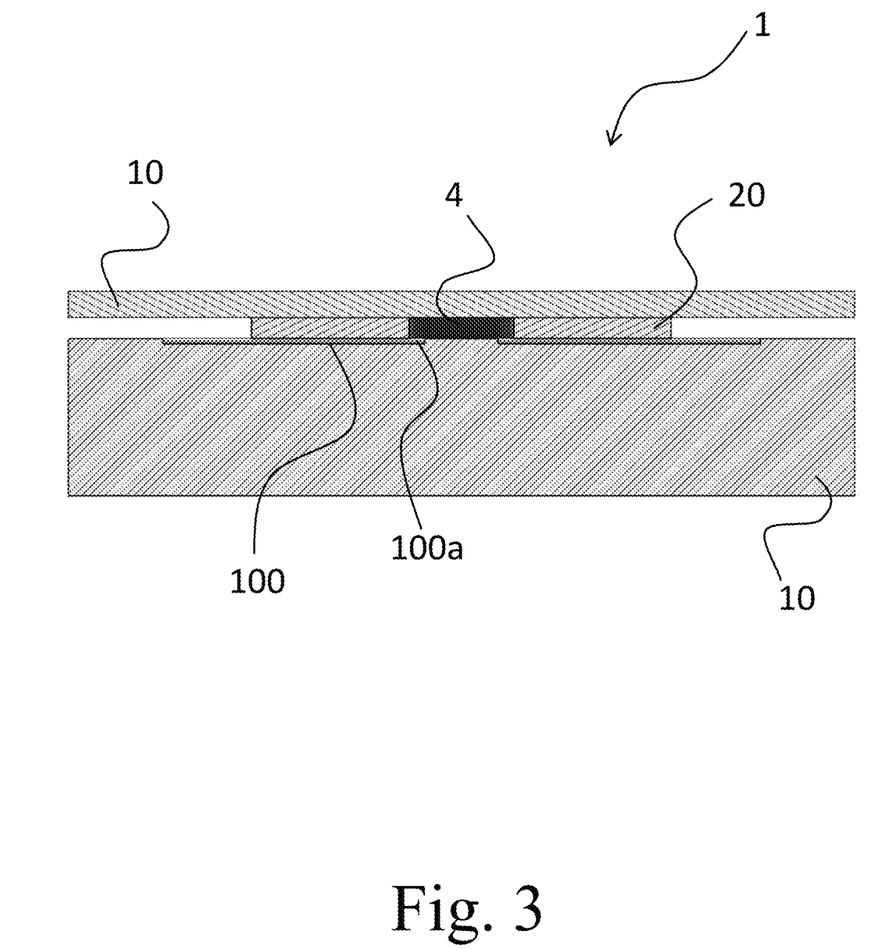
FIG. 3 shows a cross-sectional view of the medical device in which the lid and spacer of the base with the recessed part are in contact with each other, according to the present invention.

FIG. 3 shows a cross-sectional view of the medical device 1 in which the lid 30 and the spacer 20 of the base 2 with the recessed part 3 are in contact with each other. The cross-section in FIG. 3 corresponds to the cross-section in FIG. 2. By covering the recessed part 3 of the base 2 with the lid 30, a space 4 is formed. The space 4 is in fluid communication with the flow channel 100 at the inlets 100a of the flow channel 100. In the present embodiment, the space 4 is an open system in fluid communication with outside air through the flow channel 100, but the space 4 may be a closed system in which the flow channel 100 is not in fluid communication with the outside air. The space 4 in the open system allows more of the embedding material to be discharged. The space 4 in the closed system can prevent contamination from pathogens. The space 4 in the closed system can be formed, for example, by having the grooves on at least a part of the surface 10a of the spacer support 10 being in contact with the spacer 20.

The spacer support 10 may have one or more embedding material reservoirs therein, and the flow channel 100 may be connected to the one or more embedding material reservoirs. When the spacer support 10 has the one or more embedding material reservoirs therein, more embedding material can be discharged, and the size of the medical device 1 can be reduced.

Figure 4:
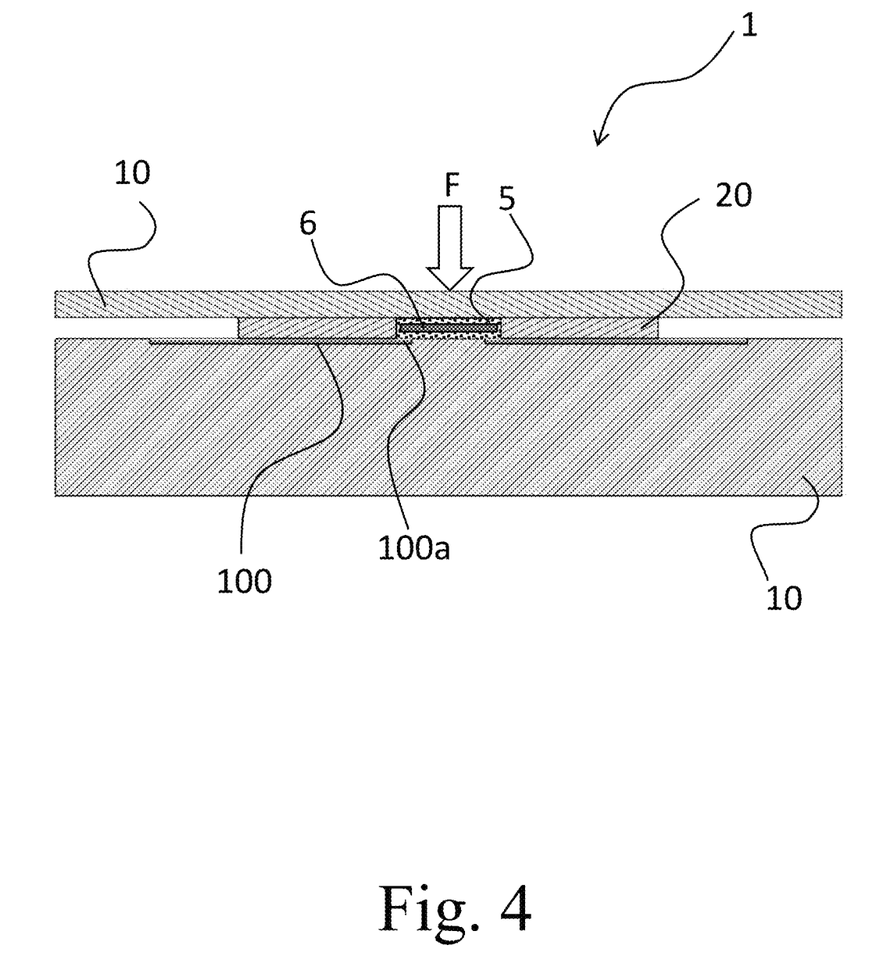
FIG. 4 shows a cross-sectional view of the medical device having a biological sample embedded by an embedding material in its space.

FIG. 4 shows a cross-sectional view of the medical device 1 having the biological sample 6 embedded by an embedding material 5 in the space 4. In the present embodiment, the flow channel 100 is configured to allow the embedding material to flow out while preventing misalignment of the biological sample 6 within the embedding material 5 when a force is applied to the medical device 1 to reduce the volume of the space 4. When the flow channel is configured in such a way, the misalignment of the biological sample 6 within the embedding material 5 can be prevented, but the position of the biological sample 6 within the embedding material 5 may be misaligned as long as it is within an acceptable range for medical transplantation. The acceptable range for the medical transplantation may be changed depending on a site where the biological sample is transplanted, and may also be changed depending on the type of the biological sample.

When a force F is applied to the medical device 1 to reduce the volume of the space 4, the biological sample 6 embedded in the embedding material 5 can be made thinner because excess embedding material flows out of the channel 100. The biological sample may be a cell sheet prepared by culture or a biological sample fragment, but not limited thereto. The biological sample may contain a scaffold material such as collagen. The embedding material should be biocompatible and can be a gel such as gelatin, hyaluronic acid, collagen, polyacrylamide gel, collagen gel, hyaluronic acid cross-linked gel, alginate gel, thermoreversible hydrogel (e.g., PNIPAM polymer) and PVA gel. The embedding material may be used to cover the entire biological sample or a portion of the biological sample (e.g., a flat or bottom surface of the biological sample). The embedding material may be a low-viscosity sol or liquid, depending on the biological sample (e.g., the biological sample containing the scaffold). When using an embedding material that hardens at low temperature and softens at room or body temperature, the embedded biological sample 6 can be solidified by cooling the medical device 1 while the force F is applied, and trimming of excess embedding material can be facilitated. When the biological sample 6 cooled and hardened with the embedding material having, for example, cylindrical shape is transplanted into biological sites with a syringe, the body temperature softens the embedding material and the shape of the biological sample 6 returns to its original shape at the biological site. The force F is preferably in the direction from the lid 30 to the biological sample 6. The force F can be generated, for example, by pinching the medical device 1 using a clip or by placing a heavy object on the lid 30.

Figure 5:
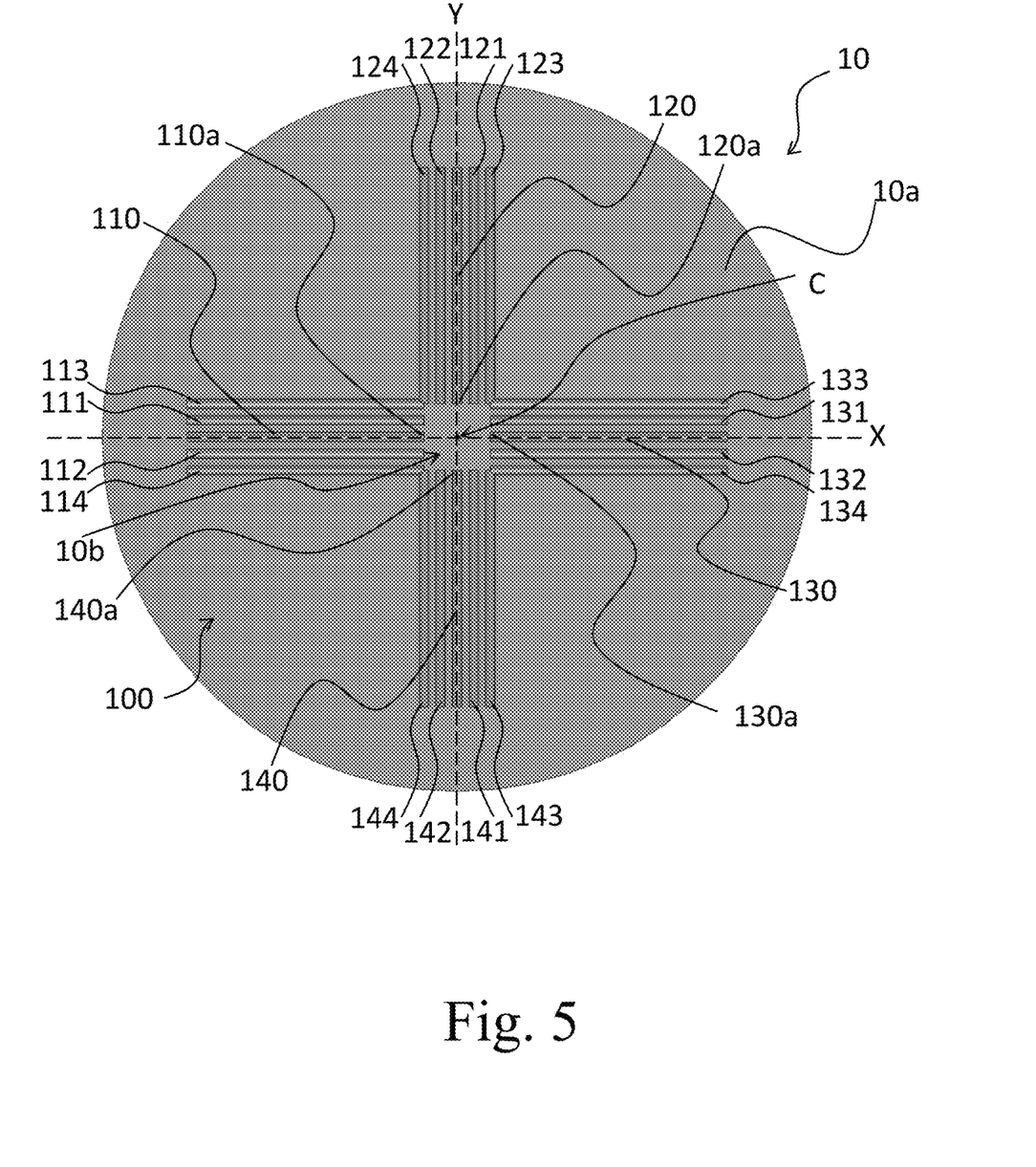
FIG. 5 shows the surface of the spacer support.

FIG. 5 shows the surface 10*a* of the spacer support 10. In the present embodiment, the flow channel 100 has four main channels (110, 120, 130 and 140) and sixteen sub-channels (111 to 114, 121 to 124, 131 to 134, and 141 to 144). For convenience of explanation, a center point C (corresponding to the center point of the bottom surface of the recessed part 3) is clearly indicated at the center of the flat part 10*b* defined by the inlets of the flow channel, and an auxiliary line X passing through the center point C and an auxiliary line Y orthogonal to the auxiliary line X and passing through the center point C are clearly indicated.

In the present embodiment, the inlets 110*a*, 120*a*, 130*a* and 140*a* of the main channels 110, 120, 130 and 140 are spaced apart at equal angles to the center point C. The number of main channels may be at least four, preferably at least four and even.

In the present embodiment, a region between two adjacent main channels contains four sub-channels. In the present embodiment, there are four regions, and each region contains the same number (i.e., four) of sub-channels.

A region between the main channel 110 and the main channel 120 includes sub-channels 111, 113, 122 and 124. A region between the main channel 120 and the main channel 130 includes sub-channels 121, 123, 131 and 133. A region between the main channel 130 and the main channel 140 includes sub-channels 132, 134, 141 and 143. A region between the main channel 140 and the main channel 110 includes sub-channels 142, 144, 112 and 114.

The main channel 110 and the sub-channels 111 to 114 are coaxially arranged with the main channel 130 and the sub-channels 131 to 134, respectively, and the main channel 120 and the sub-channels 121 to 124 are coaxially arranged with the main channel 140 and the sub-channels 141 to 144, respectively. By configuring the flow channels 100 in such a way, the excess embedding material flows out of the upper, lower, left and right channels when a force F is applied to the medical device 1 to reduce the volume of the space 4, thus preventing the misalignment of the biological sample 6 within the embedding material 5.

In the present embodiment, the flow channel 100 has the sub-channels, but it may not have the sub-channels. The arrangement of the sub-channels is not particularly limited as long as the arrangement is capable of preventing the misalignment of the biological sample 6 within the embedding material 5. For example, the arrangement may be such that the inlets of adjacent sub-channels (in some cases, the main channel and sub-channel) are equally spaced apart. The main and sub-channels are not limited to a straight shape, as long as it is possible to prevent the misalignment of the biological sample 6 within the embedding material 5. The main channel and the sub-channel and/or the sub-channel and the sub-channel may be fluidly connected by branch channels. Width of the flow channel 100 may be wide enough to prevent the biological sample 6 from flowing out.

In the present embodiment, the shape of the flat part 10*b* defined by the inlets of the flow channel, is square, but it may be other shapes such as rectangular, circular and oval. The shape of the opening of the through hole 20*a* of the spacer 20 is preferably the same as the shape of the flat part 10*b*, and the size of the opening of the through hole 20*a* of the spacer 20 is preferably larger than the size of the flat part 10*b* to the extent that the space 4 can be in fluid communication with the flow channel 100 at the inlets 100*a* of the flow channel 100.

Figure 6A:
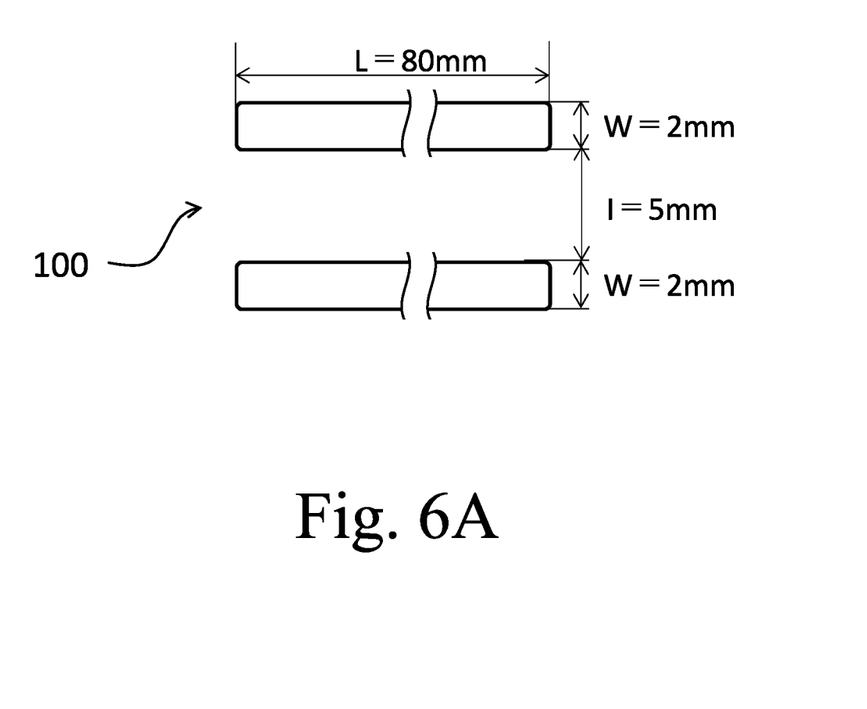
FIG. 6A shows a schematic view of the flow channels showing the dimensions and interchannel spacing of the flow channels, according to the present embodiment.
Figure 6B:
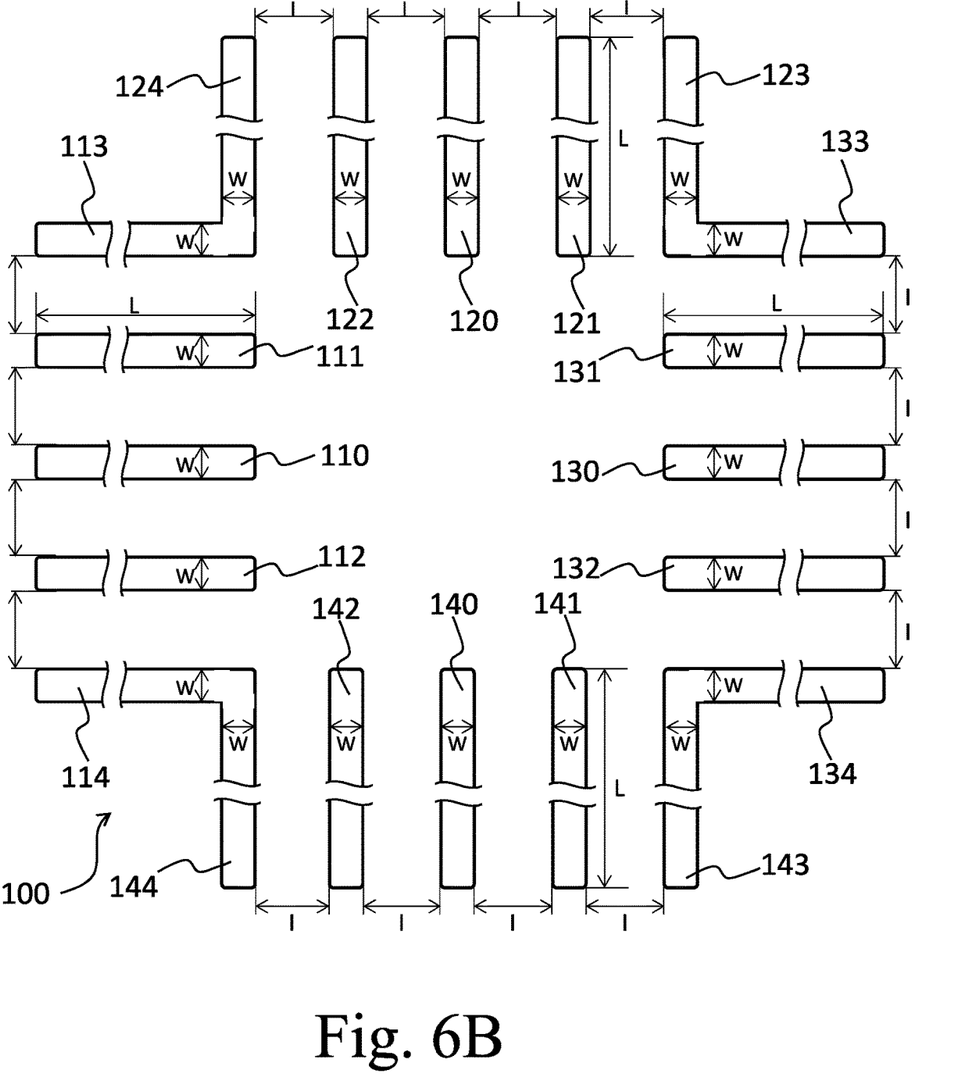
FIG. 6B shows a schematic view of the flow channels of FIG. 5 in which the dimensions and interchannel spacing shown in FIG. 6A are displayed for each channel.

FIGS. 6A and 6B are schematic diagrams of the channels showing the dimensions (L, W) and interchannel spacing I of the flow channel 100. The viewpoints in FIGS. 6A and 6B are the same as the viewpoint in FIG. 5. In FIGS. 6A and 6B, the two wavy lines on each channel indicate intermediate omissions and the spacer support 10 is omitted.

In FIG. 6A, length L of a long side of the flow channel 100 is 80 mm, length W of a short side of the flow channel 100 is 2 mm, and the interchannel spacing I is 5 mm. FIG. 6B shows an overview of the flow channels 100 of FIG. 5 in which the dimensions and interchannel spacing shown in FIG. 6A are displayed for each channel (110 to 114, 120 to 124, 130 to 134 and 140 to 144).

Figure 7:
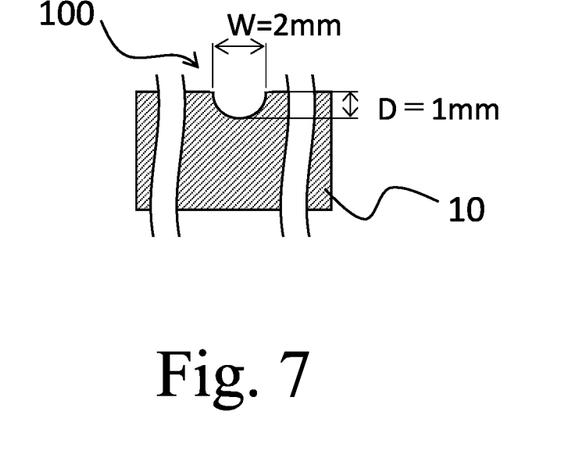
FIG. 7 shows a cross-sectional view of the flow channel from a flow direction.

FIG. 7 shows a cross-sectional view of the flow channel 100 from a flow direction. The two wavy lines on the spacer support 10 indicate intermediate omissions. In FIG. 7, depth D of the flow channel 100 is 1 mm.

The dimensions, depths, and interchannel spacing of each channel described above are illustrative and can be changed depending on the biological sample 6 and/or the number of channels. In an embodiment, the length L of the long side may be in a range between two values selected from the group consisting of 50, 60, 70, 80, 90, 100, 110, 120, 130, 140 and 150 mm, and in another embodiment, the length L of the long side may be 150 mm or more. The length W of the short side may be in a range between two values selected from the group consisting of 1.0, 1.5, 2.0, 2.5, 3.0, 3.5, 4.0, 4.5, and 5.0 mm. The interchannel spacing I between the channels may be in a range between two values selected from the group consisting of 1, 2, 3, 4, 5, 6, 7, 8, 9, and 10 mm. If an inlet of a channel overlaps an inlet of another channel, both inlets may have a common inlet.

Second Embodiment

Figure 8:
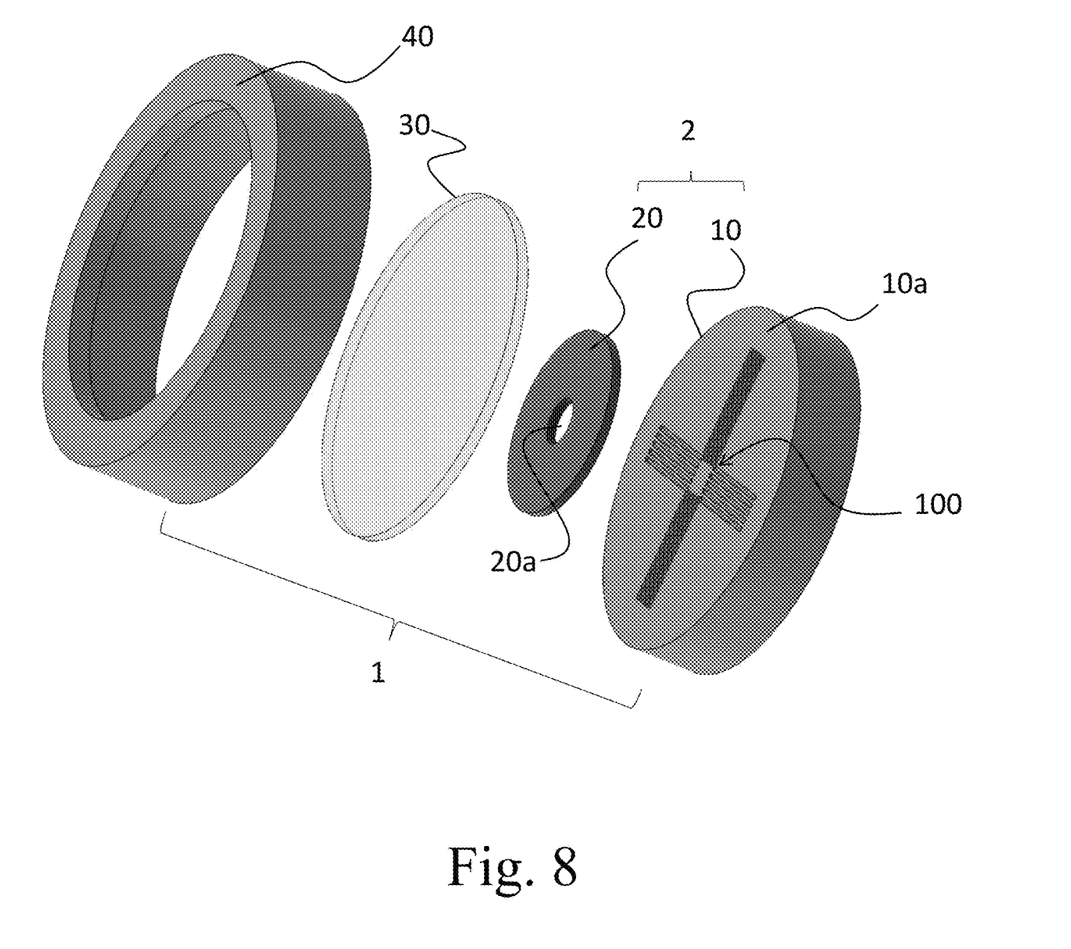
FIG. 8 shows an exploded view of a medical device with a holder.
Figure 9:
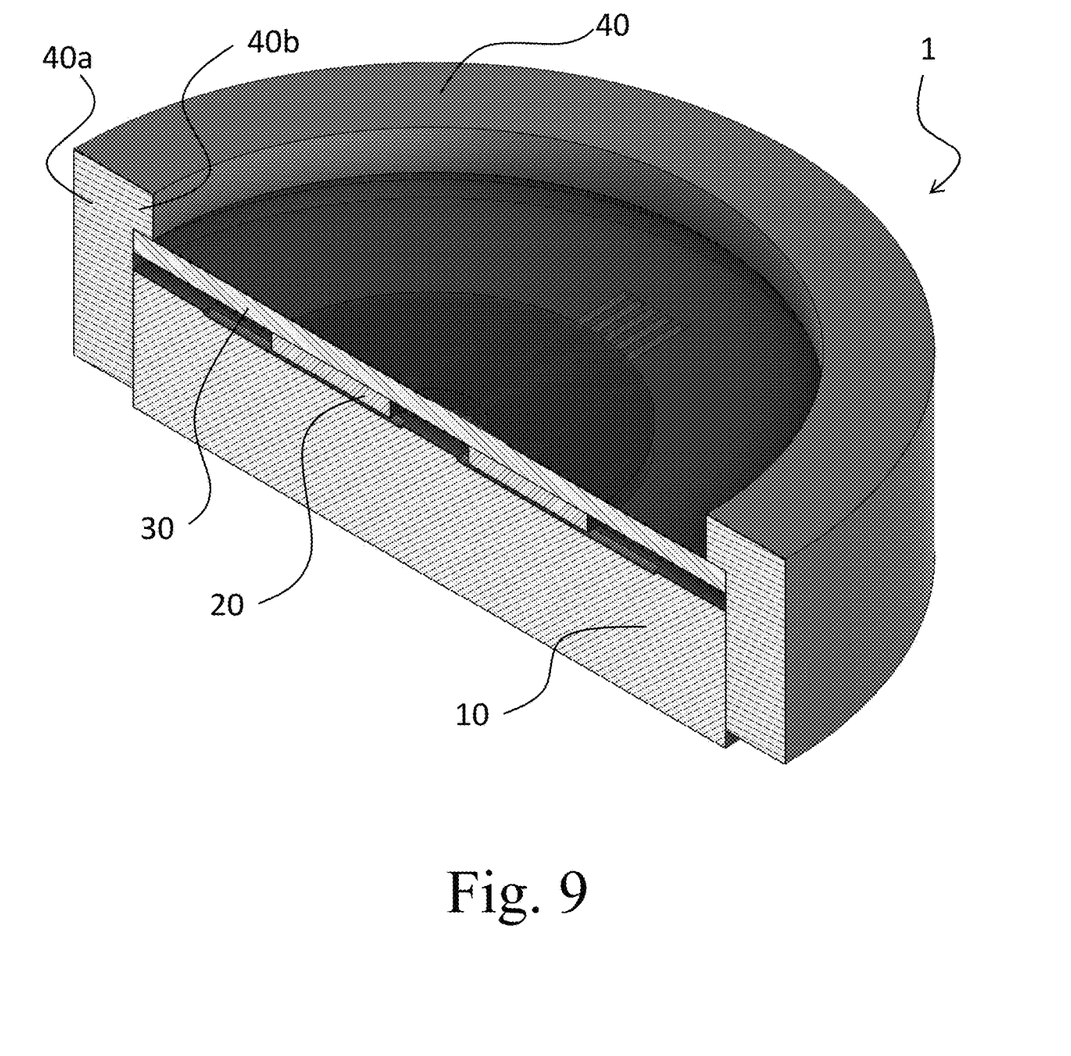
FIG. 9 shows a perspective cross-sectional view of a medical device with the holder attached.

FIG. 8 shows an exploded view of the medical device 1 with a holder 40. The holder 40 can be placed over the lid 30 to apply a uniform force F to the medical device 1. FIG. 9 shows a perspective cross-sectional view of the medical device 1 with the holder 40 attached. In this embodiment, the holder 40 is a hollow body including a straight body 40a and an overhang 40b extending toward the center of the holder 40 at the end of the straight body 40. The inner diameter of the straight body 40 is larger than the outer diameter of the spacer support 10 and the lid 30. The inner diameter of the overhang 40b is smaller than the outer diameter of the lid 30.

Third Embodiment

A method for assisting in embedding of a biological sample with an embedding material includes placing the biological sample embedded with the embedding material into a space 4 of the medical device 1; and removing excess of the embedding material by applying a force F to the medical device 1 to reduce the volume of the space 4. Necessarily, the method further includes cooling the medical device 1 while applying the force F to the medical device 1.

DESCRIPTION OF THE REFERENCE NUMERAL

1 Medical device
2 Base
3 Recessed part
4 Space
5 Embedding material
6 Biological samples
F Force
C Center point
X Auxiliary line
Y Auxiliary line perpendicular to auxiliary line X
L Length of long side of flow channel
W Length of short side of flow channel
I Interchannel spacing
D Depth of flow channel
Spacer support
10a Surface of spacer support
10b Flat part
20 Spacer
20a Through-hole of spacer
20b Inner wall of spacer
30 Lid
40 Holder
40a Straight body of holder
40b Overhang of the holder
100 Flow channel
110, 120, 130, 140 Main channel
110a, 120a, 130a, 140a Inlet of main channel
111 to 114, 121 to 124, 131 to 134, 141 to 144 Sub-channel

What is claimed is:

1. A medical device having a space for assisting in embedding of a biological sample in an embedding material, the medical device comprising:
   a lid, and
   a base with a recessed part where the space is defined by covering the recessed part with the lid,
   wherein the base comprises:
   a flow channel having inlets in fluid communication with the space,
   a spacer being in contact with the lid; and
   a spacer support being in contact with the spacer,
   the flow channel comprises at least four main channels,
   each main channel independent of each other,
   each inlet of the at least four main channels is arranged apart from each other at equal angles to a center of a bottom of the recessed part,
   the flow channel is configured to allow the embedding material to flow out while preventing misalignment of the biological sample within the embedding material when a force is applied to the medical device to reduce the volume of the space, and
   one of the following (1) and (2) is satisfied:
   (1) at least a part of a surface of the spacer support being in contact with the spacer comprises grooves, and the flow channel is defined by covering the grooves with the spacer; and
   (2) at least a part of a surface of the spacer being in contact with the spacer support comprises grooves, and the flow channel is defined by covering the grooves with the spacer support.

2. The medical device according to claim 1, wherein the flow channel comprises one or more sub-channels in each region between two adjacent main channels of the at least four main channels, and
   each region comprises the same number of sub-channels.

3. The medical device according to claim 1, wherein the spacer comprises a through hole.

4. The medical device according to claim 1, wherein the spacer is made of an elastic material.

5. The medical device according to claim 1, wherein the spacer support is made of a material with high thermal conductivity.

6. The medical device according to claim 1, further comprising a holder,
   wherein the holder is a hollow body comprising a straight body and an overhang extending toward a center of the holder at an end of the straight body,
   an inner diameter of the straight body is larger than outer diameters of the base and lid, and
   an inner diameter of the overhang is smaller than the outer diameter of the lid.

* * * * *